United States Patent [19]
Johnson

[11] Patent Number: 5,865,778
[45] Date of Patent: Feb. 2, 1999

[54] FOOTWEAR WITH INTEGRAL ANKLE SUPPORT

[76] Inventor: James F. Johnson, 246 Prairiewood Dr., Fargo, N. Dak. 58103

[21] Appl. No.: 808,002

[22] Filed: Mar. 3, 1997

[51] Int. Cl.⁶ ..................................................... A61F 5/00
[52] U.S. Cl. ................................................. 602/27; 36/88
[58] Field of Search .................................. 602/5, 16, 23, 602/27–29; 36/88, 89, 140, 144

[56] References Cited

U.S. PATENT DOCUMENTS

| | | | |
|---|---|---|---|
| 1,205,206 | 11/1916 | Hofmeister | 36/89 X |
| 1,692,896 | 11/1928 | Hilgert | 36/89 X |
| 3,834,377 | 9/1974 | Lebold. | |
| 4,771,768 | 9/1988 | Crispin | 602/27 |
| 5,086,760 | 2/1992 | Neumann et al. | 602/27 |
| 5,177,884 | 1/1993 | Rullier | 36/89 X |
| 5,183,036 | 2/1993 | Spademan | 602/27 X |
| 5,242,378 | 9/1993 | Baker | 602/23 |
| 5,250,021 | 10/1993 | Chang | 602/27 |
| 5,366,439 | 11/1994 | Peters | 602/27 |
| 5,611,773 | 3/1997 | Nash et al. | 602/27 X |
| 5,678,330 | 10/1997 | Van Dyke et al. | 36/89 |

*Primary Examiner*—Linda C. M. Dvorak
*Attorney, Agent, or Firm*—D. L. Tschida

[57] ABSTRACT

A resilient, pivoting ankle brace for conventional footwear. A lower stirrup adjusts at a mounting plate secured beneath the insole of a shoe to align to the ankle. A malleable upper stirrup pivots at a mating joint cap of the lower stirrup. A range of stirrup rotation can be set at the joint. A cushioned support collar mounts to the upper stirrup and adjustable straps retain the collar to the leg. One or more braces can be supported to the shoe to constrain foot movement. Alternative constructions of lower stirrup to mounting plate fastenings and pivot joints are disclosed. Separate stirrup and strap cushions which align to the instep and Achilles tendon are also disclosed.

19 Claims, 7 Drawing Sheets

FOOTWEAR WITH INTEGRAL ANKLE SUPPORT

BACKGROUND OF THE INVENTION

The present invention relates to therapeutic footwear and, in particular, to an improved brace adaptable to conventional footwear to support the brace and resiliently restrain the foot against excessive ankle movement in predetermined axial directions, thereby providing therapeutic support and preventing ankle injuries.

Numerous injuries are sustained annually in a variety of sports by novice and experienced sports enthusiasts. Many of such injuries arise from insufficient support at the shoe relative to the ankle. That is, the footwear either provides no support to the ligaments, bone and cartilage structure of the ankle or insufficiently supports the ankle relative to normal foot movement. Some accommodate one area of concern, but none accommodate all concerns; that is, provide a comfortable fit, correct anatomic alignment and physiologic motion.

With the exception of downhill ski boots and rollerblade boots, essentially all shoes provide a softsided shell. Some shoes include special heel and insole cushioning and liners to protect and support the foot at a preferred registration to the ground. The cushioning, however, does not particularly support the ankle or lower calf from undue forces of inversion, eversion, extension, torsion or flexion. Such forces occur with normal foot movement or from unintended stress, such as placed on the ankle in contact sports.

Applicant is aware of various solutions which have been posed to the foregoing deficiencies. Such solutions have only piecemeal addressed the involved problems, as opposed to taking an integrated approach.

Applicant is particularly aware of U.S. Pat. Nos. 260,069; 1,441,067; 1,549,382; 1,692,896; and 4,719,926 which show various metal, sectional brace assemblies. Portions of the braces are pivotally supported to articulate with respect to one another and the shoe. The braces are not fastened to the shoe. The metal braces are also susceptible to failure at the pivot joints and present problems of abrasion and structural fatigue (i.e. bending or fracture) from repeated flexion.

U.S. Pat. No. 4,621,648 discloses another brace that separately mounts to the foot and includes straps that mount to the shoe, once the braced foot is inserted into the shoe. U.S. Pat. No. 4,821,743 discloses a shoe that contains formed pockets in the liner for receiving a resin formed ankle brace. The brace extends only the height of the shoe and is restrained only by the normal shoe fasteners, i.e. shoelaces. U.S. Pat. No. 3,613,273 shows still another cushioned collar for an externally supported brace of laminated construction. The latter braces are also intended to mount to only one surface of the leg and/or require specially formed shoes.

In contrast to the known art and commercially available shoes, Applicant believes a resilient brace which is fastened to the shoe and fitted to the foot and the lower calf provides a preferable support system to control ankle stresses. Such a brace also accommodates an after-market mounting to existing footwear, such as athletic shoes. U.S. Pat. No. 5,226,875 discloses alternative brace constructions considered by Applicant which provide such support.

The subject invention improves on the foregoing braces with still other alternative constructions that facilitate the attachment of the brace to the shoe, the alignment of the brace to the foot and the control of brace movement. One or more of the present braces can be supported to a shoe and be separately aligned to the opposing lateral surfaces of the ankle. The braces also allow custom fitting of the malleoli in the AP dimensions or longitudinal axis and an adjustment for rotation which adjustments are not possible with other known braces.

SUMMARY OF THE INVENTION

It is a primary object of the present invention to provide an ankle support brace which can be mounted to conventional footwear, particularly athletic footwear.

It is a further object to provide a brace construction which is adaptable to offer either single or bilateral support in the region of the ankle and lower calf.

It is a further object of the invention to provide a brace which accommodates normal, healthy foot movement for an intended activity, yet progressively limits or controls movement in predetermined other injury producing directions.

It is a further object of the invention to retain the brace to the leg and to a mounting plate secured to the shoe and to adjust mating pivots at lower and upper stirrups to control ankle movement.

It is a further object of the invention to provide a lower stirrup to mounting plate fastening which permits fore and aft, lateral and rotational adjustment of the stirrup.

It is a further object of the invention to provide a concave pivot coupler between the upper and lower stirrups.

It is a further object of the invention to provide a concave stirrup coupler having an ability to control the relative range of motion between the upper and lower stirrups.

It is a further object of the invention to provide a cushioned collar or calf restraint which mounts to the upper stirrup and secures the brace to the leg.

It is a further object of the invention to provide preformed and malleable stirrup pieces which are shaped to align with the curvatures of the ankle and lower calf.

Various of the foregoing objects, advantages and distinctions of the invention are particularly obtained in a number of presently disclosed, preferred brace constructions which are adaptable to a variety of footwear. The braces find particular advantage with athletic footwear for court surfaces and cleated footwear for turf or grass surfaces. Depending upon the support desired, one or two braces can be mounted to a selected shoe to support the foot and ankle in a preferred alignment. Most typically, a pair of braces are mounted to support a foot.

Each brace includes a foot plate which fastens to the shoe. A lower stirrup fastens to the foot plate at a preferred alignment. Provisions are made to permit fore and aft, lateral and rotational adjustments at the lower stirrup. An upper stirrup, which mounts to the calf, mates with a concave pivot joint at the lower stirrup. The pivot joint is constructed to limit ankle rotation to a limited range within the plane of the stirrups or provide alternative fixed preset alignments.

The lower stirrup can be constructed from a nylon, molded plastic, fiberglass, metal or composite tailored to progressively flex with increasing resistance to undesired motion, yet withstand disruptive forces to fibular calcaneal ligaments and the anterior talar fibular ligament. Patterned corrugations and other stiffeners tailor the brace to provide controlled brace flexion in preferred axial directions.

The upper stirrup can be constructed of a similar material to the lower stirrup. A malleable material, such as a flexible, thermosetting plastic or metal can also be used. The elongated body of the upper stirrup is shaped to mount against the calf. A concave recess or joint back at the upper stirrup mates with a concave, joint cap at the lower stirrup. Fasteners fitted to aligned holes and slotted apertures at the joint backing and cap pieces limit rotation at the pivot.

A cushioned cuff or collar is retained to the upper stirrup and wraps around the calf. Strap fasteners and buckles secured to the collar restrain the upper stirrup to the calf.

In one construction of the lower stirrup and mounting plate, a pair of bored tangs project at approximately 90 degrees to the lower stirrup. Recessed channels at the peripheral edges of the foot plate receives the tangs. Multiple rows of apertures at a mounting surface are selectively alignable to the bores of the tangs. Suitable fasteners retain the lower stirrup to the foot plate and the foot plate to the shoe. In another lower stirrup and foot plate construction, a single bored tang projects from the lower stirrup and aligns to slotted apertures at the foot plate.

In still another lower stirrup and foot plate construction, a series of grooves are provided at the peripheral edges of the foot plate. Interlocking tongues project from an orthogonal tang at the lower stirrup and mate with selected ones of the grooves.

Detachable cushion pads are also provided and as necessary mount to the lower stirrup in the region of the instep and to the collar straps in the region of the Achilles tendon to further stabilize the brace. The foot plate can also be constructed with a flared or cupped aft surface beginning from the medial and lateral edges to form a heel cup.

Still other objects, advantages and distinctions of the invention will become more apparent from the following detailed description with respect to the appended drawings. To the extent various modifications and improvements have been considered, they are described as appropriate. The description is intended to be illustrative only of considered constructions, modifications and improvements and should not be interpreted in limitation thereto. Rather, the invention should be interpreted within the broad scope of the further appended claims. To the extent similar components or assemblies are disclosed at the various drawings like numerical designations are also provided.

DESCRIPTION OF THE PREFERRED EMBODIMENT

Figure 1:
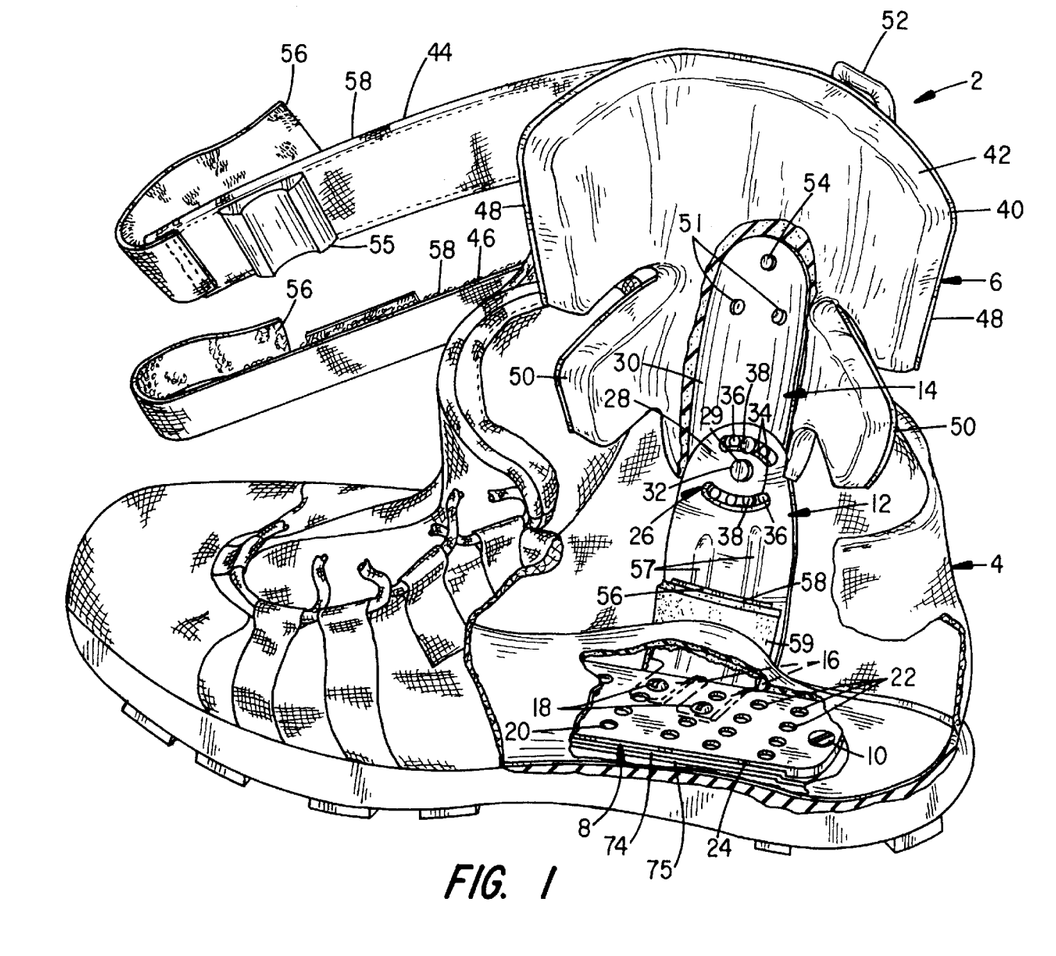
FIG. 1 is a perspective drawing shown in partial cutaway to one of the molded braces of the invention as it appears when mounted to a typical shoe as seen from the front of the brace which adjoins the ankle.

Referring to FIG. 1, a perspective drawing is shown to a brace 2 of the subject invention as it appears when mounted to a typical shoe 4. The shoe 4 can be of any construction, although most typically the brace 2 would be fitted to various athletic shoes. The brace 2 supports the ankle and calf for commonly experienced axial forces during strenuous activities. These forces can be experienced as flexion, torsion, inversion, eversion, extension and rotation.

The brace 2 is secured to the shoe 4 and to the calf at a collar 6. Although a single brace 2 is shown, a pair of braces 2 are most typically mounted to the shoe 4. In the latter instance, separate collars 6 or a single collar 6 can be used to secure the individual braces 2 to either side of the leg.

The brace 2 is designed to permit controlled motion of the leg and ankle in a preferred plane of motion and prevent motion or provide a predetermined flexion characteristic in other directions. The brace 2 flexes with progressively increasing resistance in axial directions other than the preferred plane and relative to which the brace 2 is laterally offset. The brace 2 extends from the instep or along the outside surface of the ankle upward along the sides of the calf to stabilize the ankle and the lower regions of the tibia relative to the shoe 4.

The brace 2 includes a foot plate 8 which is fastened to the sole and/or heel of the shoe 4 with a suitable type of fastener 10, e.g. screws, rivets, hook and loop or VELCRO fasteners, adhesive strips or an adhesive alone. Alternative screw fasteners 10 and full length, mating VELCRO strips 74, 75 are both shown, see also FIG. 3. The length and configuration of the strips 74, 75 are normally cut to mate with the lower surface of the foot plate.

Secured to the foot plate 8 are lower and upper stirrups 12 and 14. The upper stirrup 14 is shown in cutaway. The lower stirrup 12 is secured to the foot plate 8 at a pair of tangs 16 (shown in dashed line) with fasteners 18. One of a pair of apertures 20 at each tang 16 is aligned to an appropriate aperture 22 of a number of rows of apertures 22 formed in a peripheral edge channel space 24 of the foot plate 8. The channel space 24 and apertures 22 permit fore and aft and lateral adjustment of the lower stirrup 12, as well as partial rotation of the lower stirrup 12 relative to the foot plate 8.

Rotational adjustment is accommodated by aligning the aperture 20 of one of the tangs 16 to an aperture 22 adjacent the peripheral edge of the foot plate 8 and aligning the other aperture 20 to an aperture 22 of the next adjacent interior row. Although a pair of apertures 20 are shown at each tang 16, additional apertures can be provided to permit greater lateral and rotational adjustment of the lower stirrup 12. The shape of the tangs 16 may also be adjusted as desired or a single tang 16 may be provided.

The upper stirrup 14 is secured to the lower stirrup 12 at a pivot joint 26. A concave joint cap 28 is formed into the upper end of the lower stirrup 12 and a mating concave joint back 30 is formed into the lower end of the upper stirrup 14. The joint cap and back 28 and 30 are presently configured as mating hemispherical recesses, although other shapes might be adapted to the stirrups 12, 14.

A pivot pin 32 secures the joint cap 28 and back 30 to each other at aligned center apertures 29 and 31. Provided above and below the pivot pin 32 at the joint cap 28 are a pair of arcuate slots 34. Two series of arcuately arranged holes 36 are provided at the adjoining joint back 30, see also FIG. 2.

Figure 2:
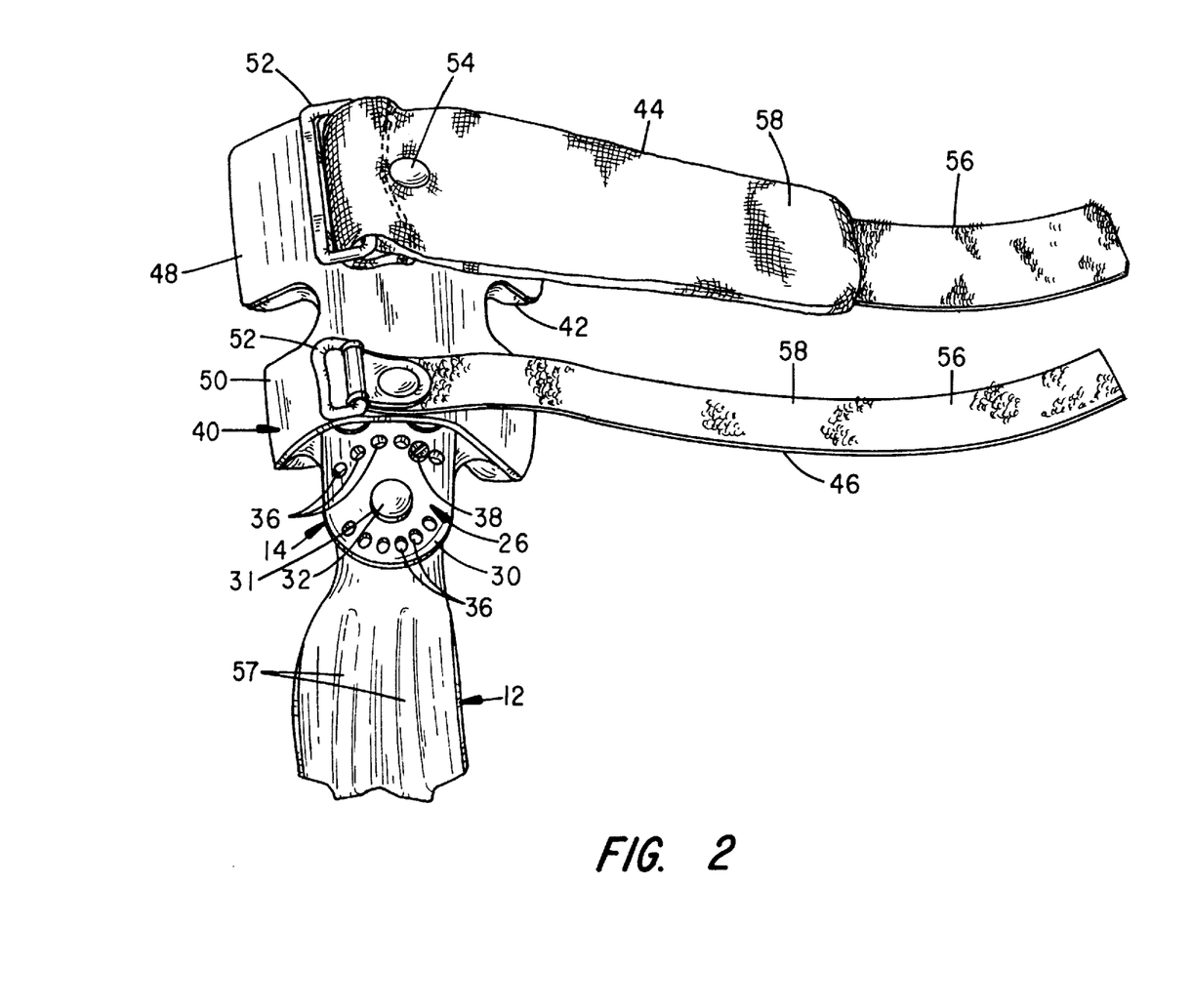
FIG. 2 is a partial plan view to the brace of FIG. 1 as seen from the rear of the brace or side of the foot.

With the mounting of one or more suitable fasteners 38 through the slots 34 and to selected ones of the holes 36, a desired range of motion is permitted between the upper and lower stirrups 12, 14. The fasteners 38 essentially serve as stops to rotational movement to provide locked (i.e. no relative stirrup movement), full or limited partial rotation. A maximum limited range of plus/minus 20 degrees is presently provided. Several smaller ranges with ten degree incremental ranges are also possible, depending upon the mounting of the fasteners 38 at the holes 36. Non-symmetrical ranges (i.e. controlled rearward and forward motion) are also possible. Other desired movements might also be accommodated with adjustment at the joint cap 28 and joint back 30.

The stirrups 12 and 14 are both formed of a molded plastic, nylon or resin based polymer. Polymers which exhibit desired shape retention and flexion resistant properties are orthoplast, alloplast, polypropylene, kevlar™ etc. Various metals and fibrous composites, such as fiberglass may also be used. For example, the upper and/or lower stirrups 14 and 12 may also be formed from a malleable, flexible metal or similar material, e.g. aluminum or a resin coated metal, which permits the forming of the stirrup to a preferred shape, yet allows the stirrup to flex. Combinations of metals and composites may also be used. Woven filaments or stranded materials may also be added to directionally stabilize the brace either vertically, radially or otherwise, for the typically anticipated forces.

By varying the composition and/or thickness of the brace material, the ankle of the wearer is stabilized against undue inversion, eversion, flexion, torsion, extension and rotation which can result from many sporting activities. Normal foot movement is otherwise not compromised, since the ball of the foot and toes are uninhibited relative to the shoe and are able to accommodate related foot movement for the activity.

Stiffeners and other materials can be added to the stirrups 12 and 14 to vary the composition and rigidity of the brace 2 to selectively tailor the brace 2 to accommodate certain types of sports activities and preferred, healthy foot movements. Corrugations are provided at the present brace to this end and are described below.

Secured to the upper stirrup 14 above the joint back 30 is the cushioned collar 6. The collar 6 is constructed of a polyethylene cuff 40, calf cushion 42 and a pair of mating straps 44 and 46. Wings 48 and 50 at the cuff 40, which are complemented at the cushion 42, wrap about the calf and spread the support of the straps 44, 46 over a larger area. The cuff 40 is secured to the upper stirrup 14 with fasteners 51, such as rivets or screws.

The cushion 42 can be constructed from a variety of solid foam materials or covered cushions. Resilient inserts which might include air, liquid or gel filled envelopes or a variety of other materials can be supported within the cushion 42. A relatively dense, semi-compressible or resilient cushion is particularly desired to cushion the calf from the relatively stiff upper stirrup 14. Upon enveloping the end of the stirrup 14, the collar 6 protects the calf from possible chaffing or abrasion.

The straps 44, 46 and associated buckles 52 are separately secured to the cuff 40 with rivets 54. The straps 44, 46 can be constructed of any variety of materials and may also be cushioned. The straps 44, 46 presently include lengths of hook and loop fastener material 56 and 58 (i.e. VELCRO) which are mounted to overlap one another to secure the brace 2 to the leg. A variety of other conventional buckles and fasteners might alternatively be used. More of the details to the construction of the pivot joint 26 and straps 44, 46 are shown at FIG. 2.

Separately attached to one or both straps 44, 46 is a shaped foam cushion 55 which aligns with the Achilles tendon. The cushion can be used or not as desired. The cushion 55 is backed with a VELCRO fastener which mates to a mating fastener strip secured to the strap 44. A separate instep cushion 59 is attached to the lower stirrup 12 with sections of hook and loop fasteners 56, 58 secured to the stirrup 12 and cushion 59. The cushions 55, 59 enhance the brace support and reduce possible abrasion.

Also more apparent from FIG. 2 are a number of vertical corrugations 57 at the lower stirrup 12 which add strength to the stirrup 12. Corrugations 57 can be provided at either the upper or lower stirrups 14, 12 to any desired pattern to add rigidity and controlled flexion and resistance to bending. The body of the stirrups 12 and 14 otherwise are formed to exhibit a concave recess that extends longitudinally over the length of the stirrups 12 and 14 to accommodate the shape of the leg and closely mount against the leg.

Figure 3:
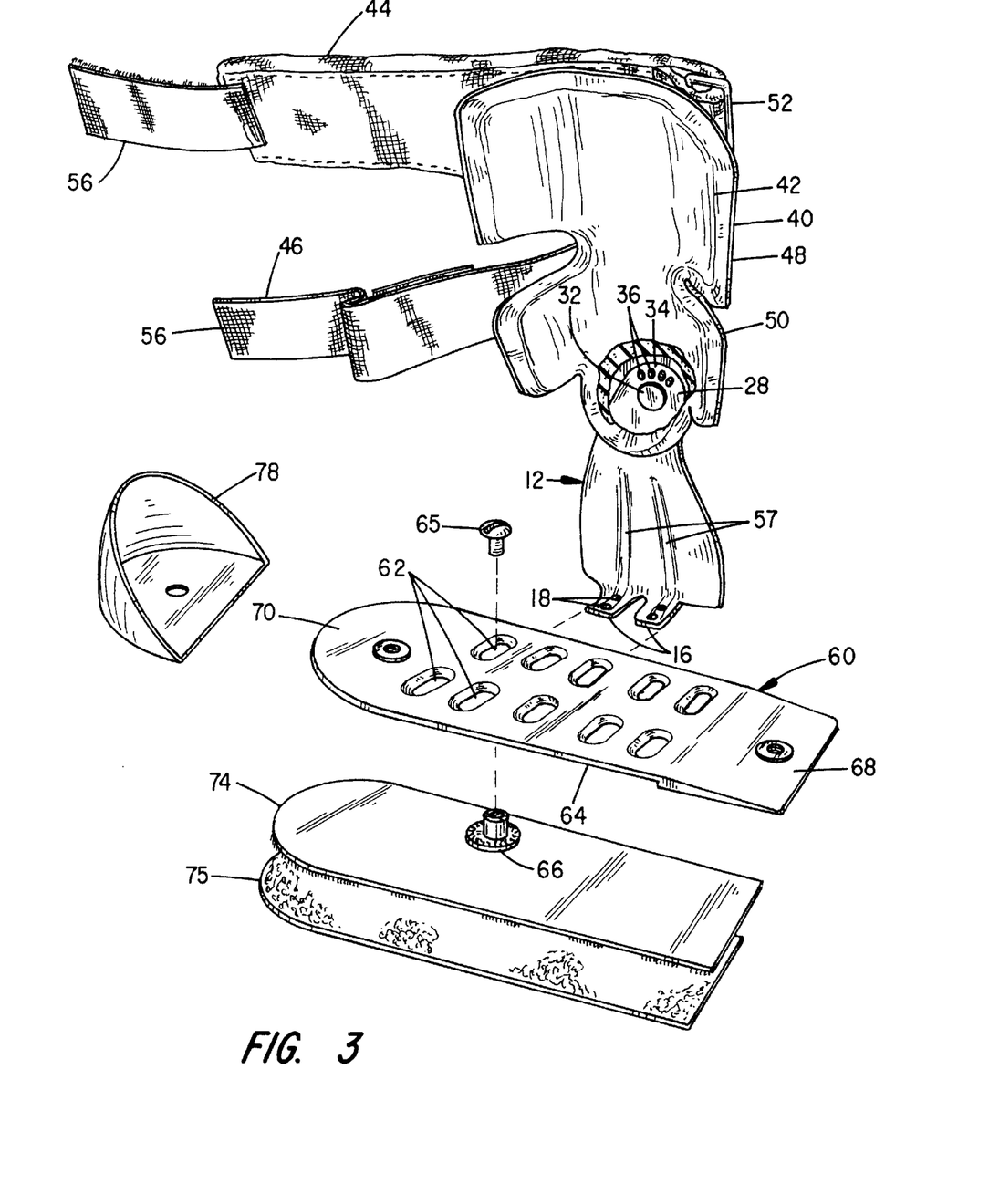
FIG. 3 is a perspective drawing shown in exploded assembly and partial cutaway to a first alternative brace.

FIG. 3 depicts an exploded assembly view to the brace 2 mounted to an alternative foot plate 60. The foot plate 60 includes two rows of countersunk slots 62 which communicate with a bottom channel space 64. Each of the tangs 16 are selectively secured to the slots 62 with a threaded fastener 65 and mating nut 66. A tapered fore end 68 mounts beneath the instep and a rounded aft end 70 mounts beneath the heel. Mating lengths of hook and loop fastener material 74, 75, such as VELCRO, semi-permanently secure the foot plate 60 to the shoe 4. The fasteners 74, 75 can extend either full length or only beneath the portions of the foot plate 60 that contact the insole. The fastener material 75 is normally adhesively bonded to the insole, although can be secured with other fasteners. A permanent adhesive may also be used to secure the foot plate 60 to the insole.

A portion of an exemplary heel cup 78 is also shown at the foot plate 60 which can be attached to the foot plate 60 with threaded fasteners or can be molded as a part of the foot plate 60. The cup 78 might also be added to any of the other foot plates disclosed herein and may also exhibit a variety of shapes which enhance the desired ankle support. The heel cup 78 would normally be covered over with the shoe lining or a separate fabric or cushioned cover piece (not shown).

Although a specific shape of brace 2 is shown, it is to be appreciated a variety of differing brace shapes can be constructed to accommodate the differing sizes and mountings necessary to the opposite sides of the ankle and attendant bone and cartilage structure. The width, length and contours of the stirrups 12 and 14 can therefore be varied, as necessary, to best fit a desired foot surface.

Figure 4:
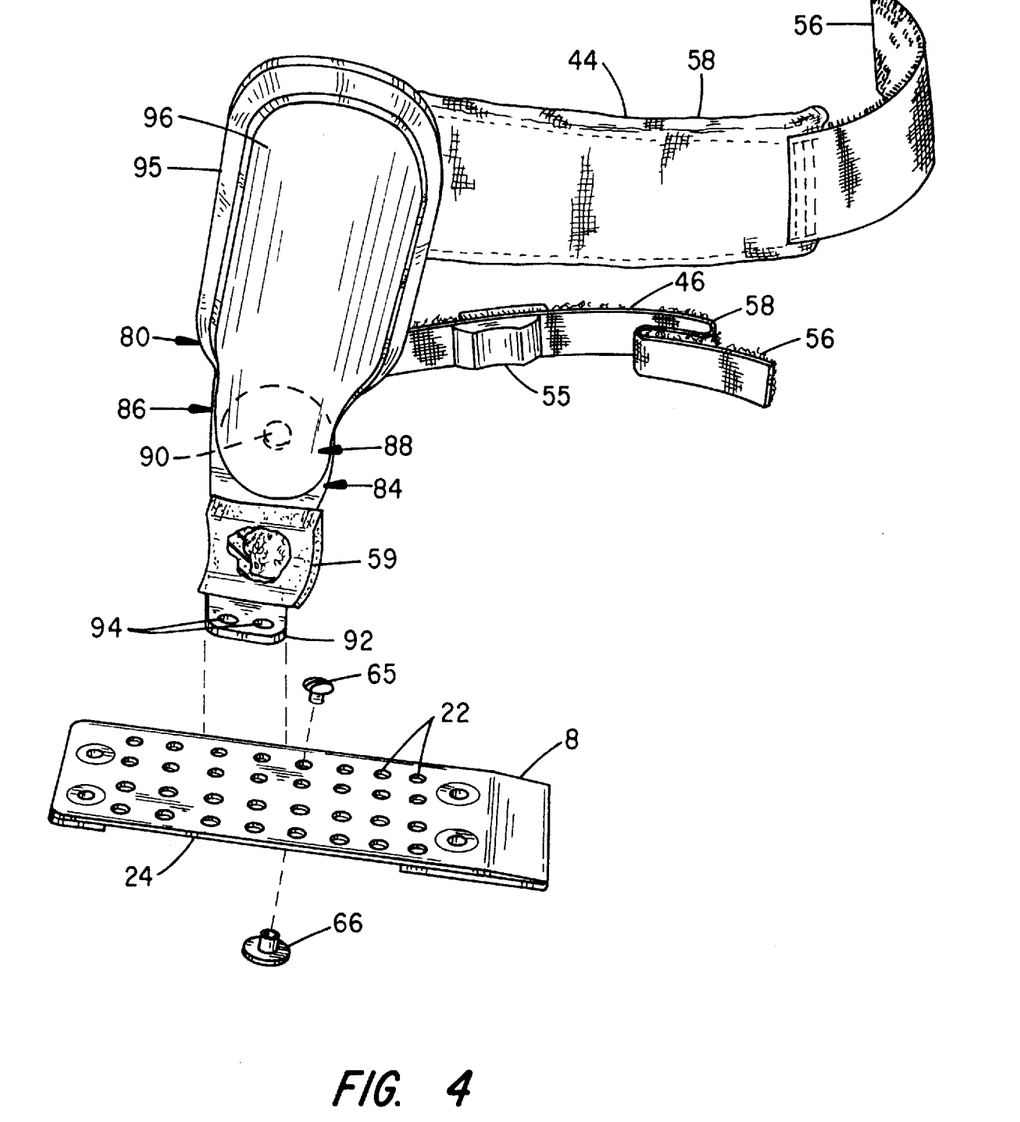
FIG. 4 is a perspective drawing shown in exploded assembly to a second alternative brace.
Figure 5:
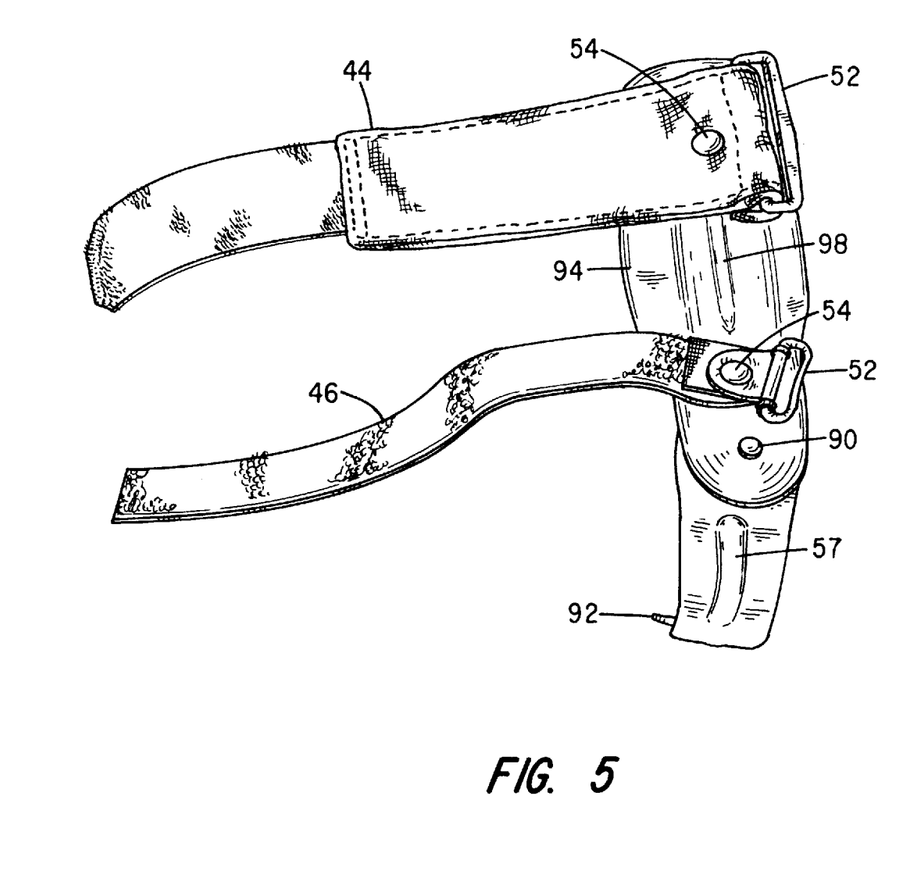
FIG. 5 is a rear plan view to the brace of FIG. 4.
Figure 6:
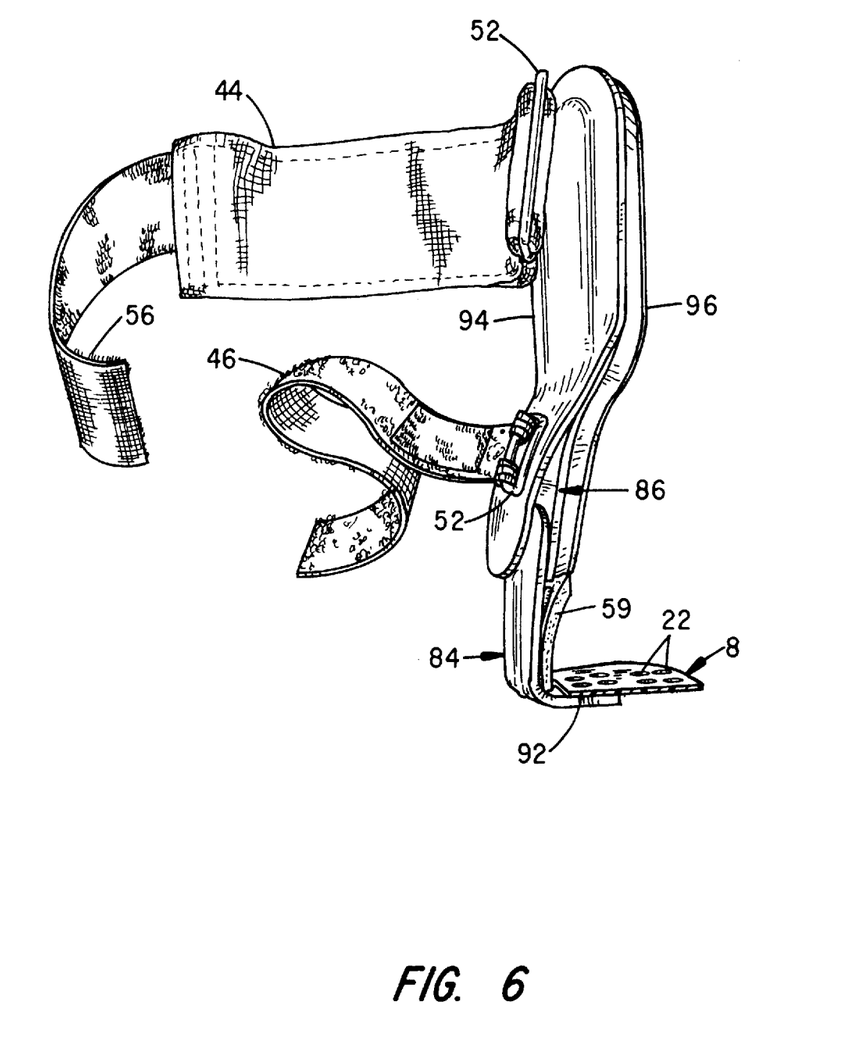
FIG. 6 is a left side perspective view to the brace of FIG. 4.

FIGS. 4, 5 and 6 depict another alternative brace 80 fitted to the foot plate 8 and wherein stirrups 84 and 86 exhibit a reduced width. The brace 82 is generally constructed in the same fashion as the brace 2. The lower and upper stirrups 84 and 86 mate at a pivot joint 88, and rotate about a pivot at a pin 90. A single tang 92 having a pair of holes 94 extends from the lower stirrup 84. The tang 92 mounts beneath the recess 24 of the foot plate 8 and is appropriately captured to selected apertures 22 with threaded fasteners 65, 66.

A rigid cuff 95 and cushion 96 are secured to the upper stirrup 86. Straps 44, 46, buckles 52 and cushion 55 wrap around the cuff 94 to retain the brace 80 to the leg. A single corrugation 57 is provided at the lower stirrup 84, reference FIG. 5. A separate longitudinal corrugation 98 is provided at the upper stirrup 86 to control flexion.

Figure 7:
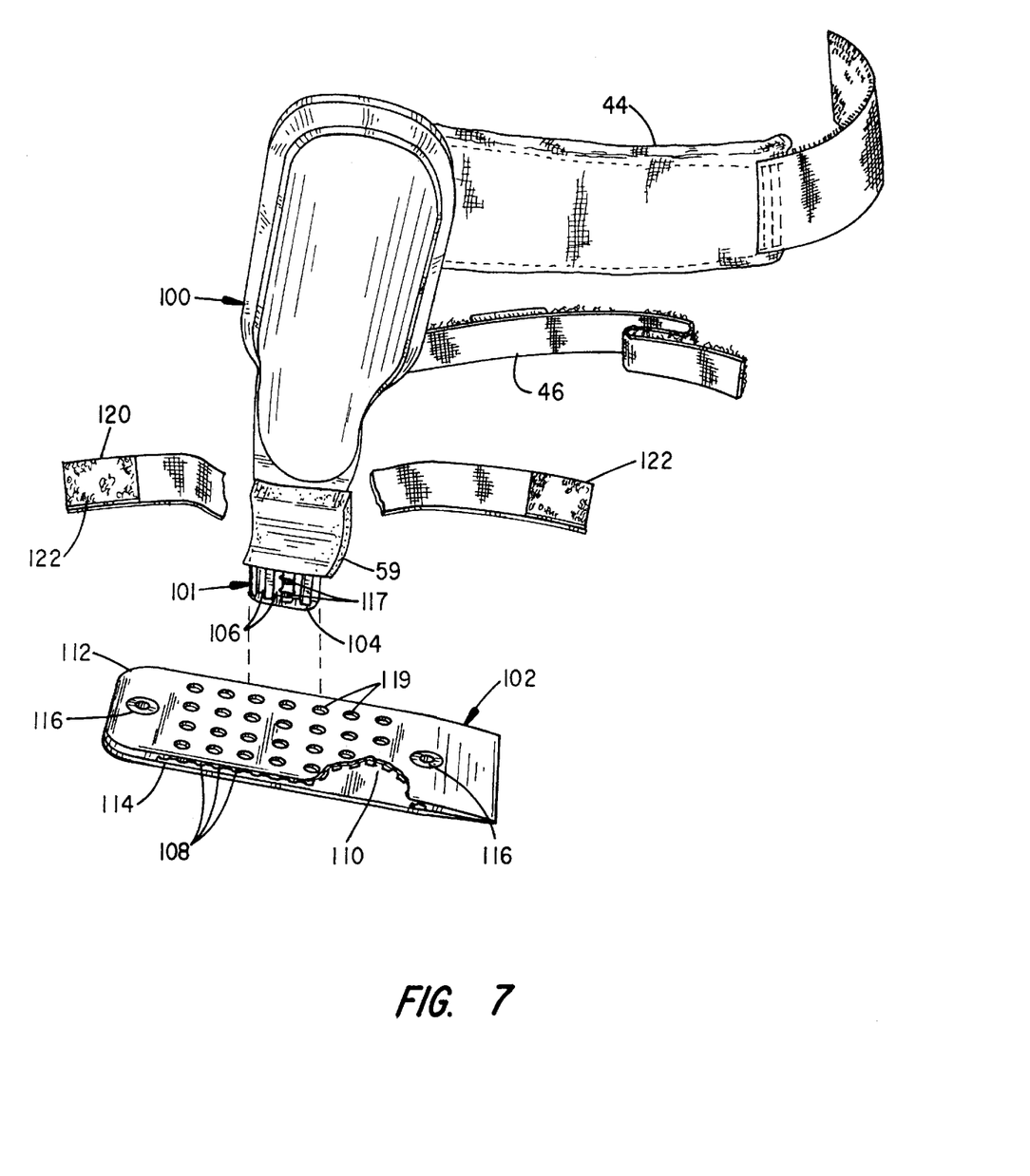
FIG. 7 is a perspective drawing show in exploded assembly to a third alternative brace.

FIG. 7 depicts a brace 100, similar to the brace 80, in exploded assembly relative to an alternative foot plate 102. A tang 104 of the lower stirrup 101 includes a series of raised tongues 106 which align to grooves 108 provided at a channel 110 of the foot plate 102. The channel 110 extends the entire width of the foot plate 102 and is defined between top and bottom plates 112, 114. Fasteners (not shown) mount through countersunk holes 116 to secure the foot plate 102 to the shoe 4.

The profile of the mating tongue 106 and grooves 108 can be varied as desired, e.g. a dovetail configuration may also be used. Apertures 117 and 119 can also be formed in the tang 104 and foot plate 102 to fix the lateral displacement of the lower stirrup 101 relative to the plate 102.

Presently, the braces 2, 80 and 100 are secured to the shoe only at the sole. However, they may also be secured to the interior shoe liner with one or more straps 120 and a number of hook and loop fastener tabs 122 secured to the strap 120 and liner. For such a mounting, the strap 120 is cinched over the lower stirrup 101. The shoe 4 may also be modified to provide slots through the liner and sidewall to receive the brace at the interior of the shoe. A strap similar to the straps 44, 46 might also be fitted to the brace and mount through slots at the shoe to further contain the brace to the shoe 4.

The invention has been described with respect to a number of considered alternative constructions, and various considered modifications and improvements thereto. It is to be appreciated, however, that still other modifications and improvements may suggest themselves to those skilled in the art. Accordingly, the following claims should be interpreted to include all those equivalent embodiments within the spirit and scope thereof.

What is claimed is:

1. Ankle support apparatus comprising:
   (a) a foot plate including means for securing said foot plate to the sole of a shoe;
   (b) a brace including lower and upper stirrups, wherein said upper stirrup rotates relative to said lower stirrup at a pivot pin, wherein means coupled between said lower and upper stirrups limit the rotation of said upper stirrup, wherein said lower stirrup includes a tang which projects substantially orthogonal to said lower stirrup and mounts to said foot plate, wherein said tang and said foot plate each include a plurality of apertures which align to one another and means for fastening said tang to said foot plate at aligned apertures, whereby the tang can be adjusted relative to said foot plate and shoe; and
   (c) collar means fitted to said upper stirrup for restraining the brace to the calf.

2. Apparatus as set forth in claim 1 wherein the lower and upper stirrups pivot at mating concavities, wherein a plurality of holes are provided at one of the concavities and a slot is provided at the other concavity and including means which selectively mounts to said holes and slot to restrict the range of rotation of the upper stirrup relative to the lower stirrup.

3. Apparatus as set forth in claim 1 including a cushion fitted to said lower stirrup to abut the foot.

4. Apparatus as set forth in claim 1 wherein said collar means includes a cushion fitted to abut the Achilles tendon.

5. Apparatus as set forth in claim 1 wherein said tang mounts at a channel space of said foot plate.

6. Apparatus as set forth in claim 1 wherein a plurality of tangs project from said lower stirrup and wherein each tang includes a plurality of apertures which align to the plurality of apertures at said foot plate.

7. Apparatus as set forth in claim 1 wherein said tang includes a plurality of projections and said foot plate includes a plurality of grooves at a recessed channel space, which projections and grooves interlock with one another.

8. Apparatus as set forth in claim 1 wherein said upper and lower stirrups include corrugations which control flexion.

9. Apparatus as set forth in claim 1 wherein hook and loop fasteners secure said foot plate to the shoe.

10. Apparatus as set forth in claim 1 wherein said collar means includes a plurality of straps.

11. Apparatus as set forth in claim 1 wherein said foot plate includes a heel cup.

12. Ankle support apparatus comprising:
   (a) a foot plate including means for securing said foot plate to the sole of a shoe and wherein a plurality of apertures extend through a surface of the foot plate above a channel space which extends along the foot plate;
   (b) a brace including lower and upper stirrups, wherein said upper stirrup rotates relative to said lower stirrup at a pivot pin, wherein means coupled between said lower and upper stirrups selectively limit the rotation of said upper stirrup, wherein said lower stirrup includes a tang having a plurality of apertures which tang projects substantially orthogonal to said lower stirrup and mounts in said channel space, and wherein fastener means aligned to said tang and foot plate restrain said tang to said foot plate, whereby the tang can be adjusted relative to said foot plate and shoe; and
   (c) collar means fitted to said upper stirrup for restraining the brace to the calf.

13. Apparatus as set forth in claim 12 wherein said collar means includes a plurality of straps and wherein hook and loop fasteners secure said foot plate to the shoe.

14. Ankle support apparatus comprising:
   (a) a foot plate including means for securing said foot plate to the sole of a shoe;
   (b) a brace including lower and upper stirrups, wherein said upper stirrup rotates relative to said lower stirrup at a pivot means coupled between said lower and upper stirrups, wherein said lower stirrup includes a tang which projects substantially orthogonal to said lower stirrup and mounts in a cavity at said foot plate, wherein said tang and said foot plate each include a plurality of apertures which align to one another and means for fastening said tang to said foot plate at aligned apertures, whereby the tang can be adjusted relative to said foot plate and shoe; and
   (c) collar means fitted to said upper stirrup and having a plurality of straps for restraining the brace to the calf.

15. Apparatus as set forth in claim 14 wherein said pivot means includes means for limiting the rotation of said upper stirrup relative to said lower stirrup.

16. Apparatus as set forth in claim 14 said pivot means comprises mating concavities at the lower and upper stirrups, wherein a plurality of holes are provided at one of the concavities and a slot is provided at the other concavity and including means which selectively mounts to said holes and slot to restrict the range of rotation of the upper stirrup relative to the lower stirrup.

17. Apparatus as set forth in claim 14 wherein hook and loop fasteners secure said foot plate to the shoe.

18. Apparatus as set forth in claim 14 wherein said collar means includes a plurality of straps.

19. Apparatus as set forth in claim 14 wherein said foot plate includes a heel cup.

* * * * *